(12) United States Patent
Monkhouse et al.

(10) Patent No.: US 6,455,567 B1
(45) Date of Patent: Sep. 24, 2002

(54) METHOD OF TREATMENT

(75) Inventors: Kathryn Louise Monkhouse, Sandwich (GB); Paul Gupta, Sandwich (GB); Shirley Jones, Sandwich (GB); Juan Lahuerta, Sandwich (GB); Gillian Christine Land, Sandwich (GB); Susan Frances Robson, Sandwich (GB); Gillian Mary Samuels, Sandwich (GB); Alan Brian Wilson, Sandwich (GB); Martin James Wythes, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/494,222

(22) Filed: Jan. 27, 2000

Related U.S. Application Data

(62) Division of application No. 08/809,988, filed as application No. PCT/EP95/03965 on Oct. 5, 1995.

(30) Foreign Application Priority Data

Oct. 12, 1994 (GB) ................................. 9420529

(51) Int. Cl.[7] ............................. A61K 31/40
(52) U.S. Cl. .................. 514/414; 514/323
(58) Field of Search .................. 514/323, 414

(56) References Cited

U.S. PATENT DOCUMENTS

| | | | |
|---|---|---|---|
| 5,409,941 A | 4/1995 | Nowakowski | 514/339 |
| 5,498,626 A | 3/1996 | Macor et al. | 514/414 |
| 5,502,065 A | 3/1996 | Brown | 514/319 |
| 5,545,644 A | 8/1996 | Macor et al. | 514/323 |
| 5,559,129 A * | 9/1996 | Macor et al. | 514/323 |
| 5,559,246 A | 9/1996 | Macor et al. | 548/468 |
| 5,578,612 A | 11/1996 | Macor et al. | 514/323 |
| 5,594,014 A | 1/1997 | Macor et al. | 514/364 |
| 5,607,951 A | 3/1997 | Macor et al. | 514/414 |
| 5,607,960 A | 3/1997 | Wythes | 514/414 |
| 5,618,834 A | 4/1997 | Butler | 514/414 |
| 5,639,752 A | 6/1997 | Macor et al. | 514/245 |
| 5,639,779 A | 6/1997 | Wythes et al. | 514/414 |
| 5,747,501 A | 5/1998 | Macor et al. | 514/376 |
| 5,770,611 A | 6/1998 | Brown | 514/323 |
| 5,886,008 A | 3/1999 | Macor et al. | 514/303 |
| 5,912,357 A | 6/1999 | Blagg et al. | 548/454 |
| 5,942,524 A | 8/1999 | Macor et al. | 514/539 |

FOREIGN PATENT DOCUMENTS

| | | |
|---|---|---|
| GB | 2222768 | 3/1990 |
| WO | 9206973 | 4/1992 |
| WO | 9320066 | 10/1993 |
| WO | 9321177 | 10/1993 |
| WO | 9321178 | 10/1993 |
| WO | 9414770 | 7/1994 |
| WO | 9424127 | 10/1994 |
| WO | 9606842 | 5/1995 |

OTHER PUBLICATIONS

Nadel, J.A., Eur. Repir J. 1998, 12:1250.
Urology 1999, 53: 239.
Quartara, L., Neuropeptides, 1998 32:1.
Nohr, D., Neuroscience, 1999, vol. 93: pp. 759–773.
Scholzen, T. E., J. Investigative Dermatology, 1999, vol. 4:55.
McCall, R. B., Journ. Pharmacology & Experimental Therapeutics, 1994, vol. 271:875.
Van de Kar, L. D. Clinical & Experimental Pharmacology & Physiology, 1996, vol. 23:166–170.
Barnes, P.J., Trends in Pharm. Sci., 1990, vol. 11:185–189.
Kajekar, R., Brit J. Pharmacol., 1995, vol. 115: 1–2.
Caekebeke, *Cephalalgia*, 13(6).
Hannerz, et al., *Headache*, 32(8), 884–89 (1992).
Hillier, et al., *Brit. J. Pharmacol.*, 112, 102P (1994).
Lee, et al., *Brain Res.*, 626, 303–305 (1993).
Le Pard, et al., *Soc. Neurosci. Abs.*, 19(1–3), 962, 394.4 (1993).
Tack, et al., *Gastroenterology*, 108 (4 suppl.), A696 (Apr. 1995).
Verleden, et al., *Eur. Respir. Jour.*, 7(18), 284s, 1324 (1994).

* cited by examiner

*Primary Examiner*—Dwayne C. Jones
(74) *Attorney, Agent, or Firm*—P. C. Richardson; P. H. Ginsburg; A. D. Joran

(57) ABSTRACT

The invention provides the use of a compound of formula (I)

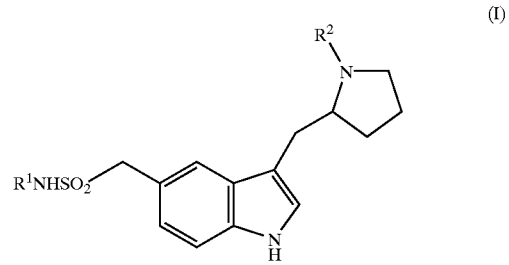

wherein $R^1$ and $R^2$ independently represent H or $C_1-C_6$ alkyl, or a pharmaceutically acceptable salt thereof, in the manufacture of a medicament for the treatment of dermatological disorders; peripheral neuropathies; arthritis; gastrointestinal or urogenital diseases; headache associated with substances or their withdrawal; tension headache; pediatric migraine; post-traumatic dysautonomic cephalgia; orofacial pain; allergic or chronic obstructive airways diseases; glaucoma or ocular inflammation; or prophylaxis of migraine.

8 Claims, No Drawings

METHOD OF TREATMENT

This application is a division of Ser. No. 08/809,988 filed on Apr. 11, 1997, which is a 371 of PCT/EP95/03965 filed on Oct. 5, 1995.

This invention relates to new uses of certain indole derivatives in the treatment or prophylaxis of medical disorders.

International Patent Application WO 92/06973 discloses a series of indole derivatives which are potent serotonin (5-HT) agonists. These compounds are useful for treating disorders arising from deficient serotonergic neurotransmission comprising hypertension, depression, anxiety, eating disorders, obesity, drug abuse, cluster headache, migraine, pain and chronic paroxysmal hemicrania and headache associated with vascular disorders. The compounds covered by WO 92106973 include (R)-5-(methylaminosulphonylmethyl)-3-(N-methylpyrrolidin-2-ylmethyl)-1H-indole (Example 5A, known as CP-122,288) and (R)-5-(methylaminosulphonylmethyl)-3-(pyrrolidin-2-ylmethyl)-1H-indole (Example 6A, known as CP-122,638).

It is known that CP-122,288 and CP-122,638 exhibit potency against neurogenic inflammation in dura mater [W. S. Lee and M. A. Moskowitz, Brain Research, 626 (1993), 303-305].

It has now been found that compounds of formula I,

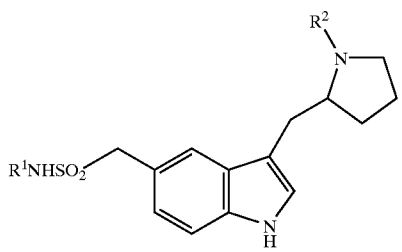

wherein $R^1$ and $R^2$ independently represent H or $C_1$–$C_6$ alkyl, and their pharmaceutically acceptable salts, are useful in a considerable number of conditions. These include:

(a) dermatological disorders, such as psoriasis; eczema; atopic eczematous dermatitis; pruritis (also known as intractable itch) including itch associated with liver cirrhosis, cancer and haemodialysis; burns; scalds; sunburn; insect bites; urticaria; and sweat gland abnormalities; bullous pemphigoid; photo-dermatoses; skin blisters; adult acne; chicken pox; and dermatitis herpetiformis;

(b) peripheral neurophathies including postherpetic neuralgia, diabetic neuropathies such as peripheral polyneuropathy and radiculopathy; causalgia and reflex sympathetic dystrophy; post-mastectomy neuralgia; post-surgical neuralgia and pain; vulvar vestibulitis; phantom limb pain; thalamic syndrome (central post-stroke pain); temporo mandibular joint syndrome; metatarsalgia (Morton's neuralgia); and neurogenic pain from nerve compression caused, for example, by a prolapsed intervertebral disc or carpal and tarsal tunnel syndromes;

(c) arthritis, including osteoarthritis and rheumatoid arthritis; systemic lupus erythrematosus; fibromyalgia; ankylosing spondilitis; and tendinitis;

(d) gastrointestinal and urogenital diseases, including cystitis; gastroeso-phargeal reflux; gastritis; urge continence; inflammatory bowel disease; irritable bowel syndrome; the compounds are also effective in regulating gastrointestinal tract motility;

(e) headache associated with substances or their withdrawal (e.g. drug withdrawal); tension headache; paediatric migraine; prophylaxis of migraine; and post-traumatic dysautonomic cephalgia;

(f) orofacial pain including toothache and pain of dental origin; earache; TMJ pain (temporal mandibular joint pain); sinus pain; myofacial pain; non-arthritic and non-musculoskeletal cervical pain; mouth ulcers; Meniere's disease; and a typical facial neuralgia;

(g) allergic and chronic obstructive airways diseases including rhinitis; conjunctivitis; bronchial oedema; bronchial asthma; neurological pulmonary oedema (adult respiratory disease syndrome); anaphylaxis; and angioedema;

(h) glaucoma (also known as intra-ocular pressure) and ocular inflammation.

Thus, one aspect of the invention relates to the use of a compound of formula I, as defined above, or a pharmaceutically acceptable salt thereof, in the manufacture of a medicament for use in any one of the above-mentioned conditions.

Another aspect of the invention relates to a pharmaceutical formulation comprising a compound of formula I, as defined above, or a pharmaceutically acceptable salt thereof, in admixture with a pharmaceutically acceptable adjuvant, diluent or carrier, characterized in that the formulation is adapted for administration to the skin. As mentioned below, conventional methods may be used to prepare the topical formulation. The formulation may be adapted for administration to the skin to the exclusion of other routes of administration.

Yet another aspect relates to a method of use in any one of the above-mentioned conditions which comprises administering a therapeutically effective amount of a compound of formula I, as defined above, or a pharmaceutically acceptable salt thereof, to a patient in need of such treatment.

The compounds of formula I, as defined above, may exist as optical isomers. The invention includes all optical isomers and mixtures thereof. However, compounds of formula I having (R)-stereochemistry as shown in formula IA,

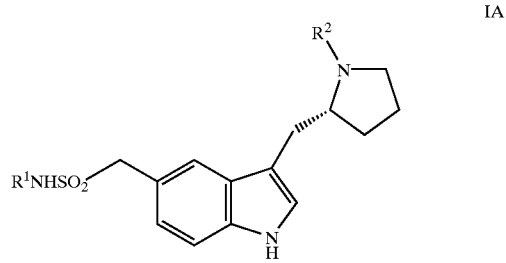

are preferred.

Alkyl groups which $R^1$ and $R^2$ may represent can be linear, cyclic or branched. However, it is preferred that $R^1$ and $R^2$ each represent methyl. Compounds of formula I include CP-122,288, CP-122,638 and (R)-5-(aminosulphonylmethyl)-3-(N-methylpyrrolidin-2-ylmethyl)-1H-indole.

The action of the compounds of formula I in preventing or alleviating the conditions mentioned above is unexpected. Some of these conditions may be treated using capsaicin [(E)-N-[(4-hydroxy-3-methoxyphenyl)-methyl]-8-methyl-4-nonenamide] which is known to antagonise neurogenic inflammation by depleting neuropeptide levels from neurones. However, the mode of action of capsaicin is totally different from that of the compounds of formula I. When administered to a patient, capsaicin selectively activates primary sensory afferents to cause the release of substances known as "SP" (substance P) and "CGRP" (calcitonin gene related peptide) which cause inflammation. The continued action of capsaicin results in the depletion of neuropeptides from the primary sensory afferents. so that these nerves lose their capacity to promote tissue inflammation. Thus, the initial action of capsaicin is generally to cause intense itching and other effects associated with neurogenic inflammation. In contrast, the compounds of formula I above suppress inflammation immediately by activating an inhibitory receptor located at the sensory nerve ending. Given this difference in function, the effects of the compounds of formula I cannot be predicted from the known effects of capsaicin; furthermore, they do not have the undesirable effects caused by the initial inflammation experienced when capsaicin in administered.

Pharmaceutically acceptable salts of the compounds of formula I include non-toxic acid addition salts, that is salts containing pharmacologically acceptable anions. Particular salts are mentioned in WO 92/06973, which also describes methods of preparing the compounds mentioned above and formulations containing the compounds for administration to patients. However, at least for oral administration, the fumarate salt is preferred.

The compounds of formula I and their salts defined above may be formulated in a conventional manner using one or more pharmaceutically acceptable carriers. Thus the active compounds may be formulated for topical, oral, buccal, intranasal, parenteral (e.g. intravenous, intramuscular or subcutaneous) or rectal administration, or in a form suitable for inhalation or insufflation. Formulation methods are described in the above-mentioned Patent Application WO 92/06973.

The daily dose of the compound administered to a patient for treatment of the above-mentioned conditions will be determined by a physician for any given patient but in general it will be typically 0.1–200 mg of active ingredient per unit oral, parenteral or buccal dose which could be administered, for example, 1 to 4 times daily for an adult weighing 70 kg). In an aerosol formulation each metered dose or "puff" may contain from 20 kg to 1000 $\mu$g of the compound and the overall daily dose will be from 100 $\mu$g to 10 mg. However, it has been found that compounds CP-122, 288 and CP-122,638 and (R)-5-(aminosulphonylmethyl)-3-(N-methylpyrrolidin-2-ylmethyl)-1-indole are active at doses several orders of magnitude less. The typical unit dose for topical, oral, buccal, intranasal, parenteral (e.g. intravenous, intramuscular or subcutaneous), rectal, inhalation or insufflation administration will then be 1 nanogram–200mg for these compounds with a correspondingly reduced dose for aerosol formulations.

The following tests are believed to give an indication of a test compound's efficacy in the majority of the conditions mentioned above:

(i) The effect of compounds of the invention in suppressing inflammation may be demonstrated by the method of Escott and Brain (*Br. J. Pharmacol,* (1993), 110, 772–776) in which oedema in the rat hind paw is measured after saphenous nerve stimulation. The test compound is administered intravenously at different amounts and the results are recorded as the ratio of plasma extravasation in the stimulated/unstimulated hind paw. It is found that compound CP 122,288 has a significant effect at administered amounts as low as $2 \times 10^{-14}$ mol/kg [Kajekar, Br. J. Pharmacol. (1995), 115,1–2].

(ii) The effect of a compound of the invention in suppressing vasodilation may be demonstrated by the method of Kajekar et al [Br. J. Pharmacol. (1995), 115, 8P] in which vasodilation in the rat hind paw is measured after saphenous nerve stimulation. The test compound is administered intravenously at different doses and the results are recorded as the change in the increase in skin blood flow. It is found that CP-122,288 has a significant effect at doses as low as $2 \times 10^{-12}$ mol/kg.

The invention is illustrated by the following examples.

Example 1

Topical Aqueous Cream Formulation

| Ingredient | Quantity (g) |
| --- | --- |
| (R)-5-(methylaminosulphonylmethyl)-3-(N-methylpyrrolidin-2-ylmethyl)-1H-indole fumarate | 0.001 g |
| Aqueous Cream BP | 999.999 g |

1 kg of Aqueous Cream BP contains emulsifying ointment (300 g), phenoxyethanol (10 g) and purified water (690 g). 1 kg of emulsifying ointment contains emulsifying wax (300 g), white soft paraffin (500 g) and liquid paraffin (200 g).

Example 2

Topical Oily Cream Formulation

| Ingredient | Quantity (g) |
| --- | --- |
| (R)-5-(methylaminosulphonylmethyl)-3-(N-methylpyrrolidin-2-ylmethyl)-1H-indole fumarate | 0.001 g |
| Oily Cream BP | 999.999 g |

1 kg of Oily Cream BP contains wool alcohols ointment (500 g), phenoxyethanol (10 g), dried magnesium sulphate (5 g) and purified water (485 g). 1 kg of wool alcohols ointment contains wool alcohols (60 g), hard paraffin (240 g), white soft paraffin (100 g) and liquid paraffin (600 g).

What is claimed is:

1. A method for treating dermatological disorders comprising administering to a mammal in need of such treatment an amount of a compound of formula I,

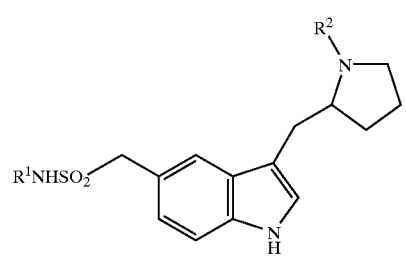

wherein $R^1$ and $R^2$ independently represent H or $C_1$–$C_6$ alkyl, or a pharmaceutically acceptable salt thereof, effective in treating such condition.

2. The method of claim 1, wherein $R^1$ and $R^2$ each represent methyl.

3. The method of claim 1, wherein the compound of formula I is in the form of its fumarate salt.

4. The method of claim 1, wherein the compound of formula I has (R)-stereochemistry as shown in formula IA,

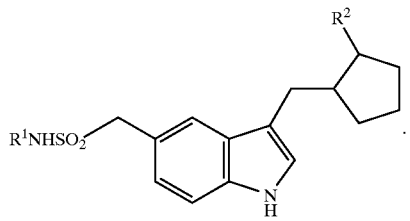

5. A pharmaceutical formulation for treating dermatological disorders comprising an amount of a compound according to claim 1 effective in treating such disorder and a pharmaceutically acceptable diluent or carrier, such that the formulation is adapted for administration to the skin.

6. A method for treating a condition selected from dermatological disorders;
which comprises administering to a mammal in need of such treatment an amount of a compound according to claim 1 effective in treating such condition.

7. The method of claim 1 wherein the dermatological disorders are selected from the group consisting of eczema, atopic eczematous dermatitis, pruritis including itch associated with liver cirrhosis, cancer and haemodialysis, burns, scalds, sunburn, insect bites, urticaria, sweat gland abnormalities, bullous pemphigoid, photo-detmatoses, skin blisters, adult acne, chicken pox, and dermatitis herpetiformis.

8. A pharmaceutical composition comprising a compound of formula 1, as defined in claim 1, or a pharmaceutically acceptable salt thereof, in admixture with a pharmaceutically acceptable adjuvant, diluent or carrier, characterized in that the formulation is adapted for administration to the skin.

* * * * *